United States Patent [19]

Salonen

[11] Patent Number: 4,849,406

[45] Date of Patent: Jul. 18, 1989

[54] METHOD FOR PROMOTING EPITHELIAL HEALING AND PREVENTION OF EPITHELIAM DESTRUCTION

[75] Inventor: Eeva-Marjatta Salonen, Espoo, Finland

[73] Assignee: Labsystems Oy, Helsinki, Finland

[21] Appl. No.: 838,339

[22] Filed: Mar. 11, 1986

[30] Foreign Application Priority Data

Nov. 22, 1985 [FI] Finland .................................. 854634

[51] Int. Cl.$^4$ .............................................. A61K 37/02
[52] U.S. Cl. ......................................... 514/8; 514/12; 514/802; 424/101
[58] Field of Search .................. 424/101; 514/802, 12, 514/8

[56] References Cited

U.S. PATENT DOCUMENTS

| | | | |
|---|---|---|---|
| 4,171,377 | 10/1979 | Green et al. | 514/561 |
| 4,377,572 | 3/1983 | Schwarz et al. | 424/101 |
| 4,592,997 | 6/1986 | Wilhelms et al. | 435/23 |

OTHER PUBLICATIONS

Heine et al., cited in Chem. Abstracts, 101:148914a 1984.
Nakagawa et al., cited in Chem. Abstracts 105:131609q 1986.
Zirm, Klin. Mbl. Augenheilk, 177 (1980) pp. 759-764.
Berman et al., Investigative Ophthamology and Visual Science, vol. 24, (1983) pp. 1358-1366.

*Primary Examiner*—John W. Rollins
*Assistant Examiner*—Jacqueline M. Stone
*Attorney, Agent, or Firm*—Hopgood, Calimafde, Kalil, Blaustein & Judlowe

[57] ABSTRACT

A method of determining the presence of epithelial lesions is provided wherein a sample of a body fluid taken from an epithelial region suspected to have said lesions is tested for the presence of a proteolytic activity. The lesion is then treated by applying a therapeutically effective amount of a proteinase inhibitor in the form of a physiologically acceptable preparation, a pharmaceutical preparation of aprotinin being particularly preferred.

7 Claims, No Drawings

METHOD FOR PROMOTING EPITHELIAL HEALING AND PREVENTION OF EPITHELIAM DESTRUCTION

This invention relates to a method for diagnosing epithelial lesions, to a method for treating such lesions, and to pharmaceutical preparations for the treatment of epithelial lesions, particularly corneal lesions.

STATE OF THE ART

It is known to treat epithelial lesions, such as corneal lesions, using local antibiotics according to sensitivity tests of conjunctival or corneal cultures. Such treatments have included the use of corticosteroids, antimicrobial agents, certain types of saline solutions, etc. Fibronectin preparations have been proposed for the treatment of corneal ulcers. In this connection, details of the state-of-the-art are given below, references being made to technical publications by way of footnotes, the publications being listed in the Appendix.

Fibronectin is a high molecular weight glycoprotein present in soluble form in blood plasma and other body fluids and in insoluble form in interstitial connective tissues and in association with many basement membranes[1-3]. Thus, in the human cornea, epithelial cells are anchored to the basement membrane fibronectin[4]. Fibronectin is well known for its multiple interactions, such as those with collagen[5], glycosaminoglycans[6,7], C-reactive protein[8], plasminogen and its activator[9] and cell surfaces[10]. Studies on embryonal models indicate that fibronectin is involved in cell migration and is found, for example, along the posterior surface of the primary corneal stroma, where corneal endothelial cells migrate[11]. Fibronectin also appears to have an organizing role in connective tissue formation, but is not prominent in mature extracellular matrices such as dentine, bone, tendon or cornea[3].

Fibronectin is quite prominent in tissue injury[12]. In lesions involving vascular injury, once thrombin is generated, a large proportion of plasma fibronectin, about one third, becomes incorporated into the fibrin clot. This is due to covalent cross-linking by thrombin-activated Factor $XIII_a$. Similarly, when epidermis is separated from the dermis by experimentally induced skin blistering, rapid deposition of fibrin and fibronectin occurs[13] and, when the rabbit cornea is wounded, fibrin and fibronectin appear[14]. Fibronectin has been suggested to promote the healing of corneal epithelial wounds by providing the attachment for regenerating epithelial cells. Shortly after corneal wounds fibrin and fibronectin are deposited on the denuded corneal surface and then progressively disappear during subsequent re-epithelialization[14]. Thus, it has been proposed that fibronectin might be useful in treating therapy-resistant corneal ulcers[15,16]. When corneal epithelial cells were scraped off, fibronectin was detected beneath the migrating epithelial cells[14]. When purified rabbit plasma fibronectin was added to the culture medium, epithelial cell migration was greatly enhanced. Conversely, migration was inhibited by the addition of guinea pig IgG anti-rabbit fibronectin[15].

Characteristic of fibronectin is its remarkable susceptibility to proteinases; this is true both for the matrix and the soluble form of the protein[17]. Thus, mild proteolytic treatment will shave off and cleave cell surface fibronectin and detach cells from their growth substratum.

A powerful means of generating wide-spectrum proteolytic activity is provided by the activation of plasminogen, a proenzyme present in large quantities in the body fluids and the extracellular space where it can be converted to plasmin by cell-derived plasminogen activators (PAs) to generate localized pericellular proteolysis. Two types of PA can be distinguished[18], based on the molecular weight and immunological reactivity, immunohistochemical distribution and amino acid sequence of the proteins. One type with approximately $M_r$ 70 000, known as tissue-type PA (t-PA) is assumed to play a role in plasminogen activation leading to thrombolysis. Another type with $M_r$ 48 000, urokinase-type (u-PA) is believed, among other functions, to play a role in certain normal and pathological processes that involve tissue degradation, such as inflammation, implantation of fertilized oocytes and tumor cell invasion. Once generated, plasmin and other activated zymogens may in turn activate latent collagenase[19,20]. Moreover, in inflammatory conditions cellular proteinases of neutrophils, macrophages and other cells involved in host defense and tissue repair are known to operate[18,21,22].

STATEMENT OF THE INVENTION

It has been discovered that tear fluids of patients with corneal inflammatory lesions contain high levels of proteolytic activity which can be inhibited by aprotinin, with or without fibronectin. This discovery has formed the basis for a new form of therapy in which a proteinase inhibitor is used in the treatment of corneal ulcers in humans, as well as in veterinary applications.

One embodiment of the invention resides in the development of a diagnosing tool for detecting the presence of epithelial lesions, such as corneal lesions, by testing a body fluid obtained from the region of the epithelial lesion for the presence of a proteolytic enzyme.

Another embodiment resides in a method for treating epithelial lesions by applying to said lesions a therapeutically effective amount of a proteinase inhibitor, e.g., aprotinin, in the form of a physiologically acceptable preparation.

A further embodiment of the invention resides in a pharmaceutical preparation for treating epithelial lesions comprising a proteinase inhibitor, such as aprotinin. The use of the invention in treating corneal lesions is described hereinafter. Tests are provided to show the effect of proteolytic activity. A similar mechanism is believed to apply to various types of lesions of skin and mucous membranes. This form of treatment, inhibition of proteolytic activity, may also be used as a prophylatic to prevent epithelial destruction.

MATERIALS AND METHODS FOR CARRYING OUT THE INVENTION

Assay of proteolytic activity in tear fluids.

Tear fluid was collected into a glass capillary. Proteolytic activity, using an 8 ul specimen of tear fluid, was measured by the radial caseinolysis procedure[23], using agarose gel and bovine milk casein as substrate. Human plasmin (20 casein units per mg; Kabi Diagnostica, Stockholm, Sweden) was used as standard. The results are expressed as micrograms of plasmin-like activity per milliliter tear fluid. Plasminogen activator levels were determined according to Saksela[23] using plasminogen-containing casein-agarose gels and urokinase (50 000 Plough units/ml; Calbiochem) as standard.

Determination of fibronectin in tear fluid.

Solid-phase enzyme immunoassay[24] was used to quantitate fibronectin antigen, and immunoblotting was used to determine the degree of its fragmentation.

Proteinase inhibitors

Aprotinin (20 000 IU/ml Trasylol[r], Bayer), L-cysteine (0.15 M; E. Merck), heparin (25000 IU/ml Medica).

Fibronectin preparation.

Fibronectin was purified from human plasma of two healthy volunteers using affinity chromatography on gelatin-agarose[5] and Sephadex G-25 gel filtration. The final preparation contained 200 ug/ml fibronectin in 0.15 M arginine-HCl buffer, pH 8.5; human serum albumin, 500 ug/ml was added as carrier protein. The preparation was devoid of proteolytic activity, was pyrogen-free, free of bacteria and chlamydia and gave negative results in attempted virus isolation. No hepatitis B virus S or HTLV-III antigen were detected. According to sodium dodecyl sulfate polyacrylamide (5-16%) gel electrophoresis (SDS-PAGE) and immunoblotting with a polyclonal anti-fibronectin rabbit serum, >95% of the fibronectin was in intact form Zymography.

Molecular weights of proteinases were determined using SDS-PAGE under nonreducing condition, extensive washing of the gel with nonionic detergent and overlaying it with casein-agarose. The lytic zones developed within 24-48 h of incubation of +37°.

Patients and control individuals.

All patients reported here were treated in the Eye Clinic of the Helsinki Central University Hospital.

Proteinase inhibitor and fibronectin treatment.

The patients received topical aprotinin (20 or 40 IU/ml), diluted from the stock preparation in sterile saline or commercially obtained wetting agent (Liquifilm Tears; Allergan), 1-2 drops (50 ul each) at 3 hour intervals. When applied, fibronectin (200 ug/ml) was administered 2-3 minutes after aprotinin treatment, also using 1-2 drops at a time.

Control individuals.

Three females and one male from the laboratory personnel and four policlinic cataract patients with no history or signs of ocular inflammatory disease served as controls (see Table 3 ). The tear fluid was collected from all individuals either by using a Pasteur pipette (spontaneous tearing) or using a 8 ul capillary tube in cases with low or normal tear secretion.

RESULTS

Detection of proteolytic activity in tear fluid and its inhibition

Within a period of four months tear fluid specimens of altogether 45 patients with corneal lesions were tested for proteolytic activity. It was found that 29 of these were positive. The distribution of the patients in the different diagnosis categories and the results of the tear fluid tests have been summarized in Table 1. The most conspicuous finding is the high proportion of patients with therapy-resistant erosion in the group with plasmin-like proteolytic activity in tear fluid. The molecular sizes of the tear fluid proteinases were determined using zymography and were found to comigrate with plasmin ($M_r$ 87 000). No such activity was seen in the zymography of the control tear fluid specimens. In order to clarify whether the plasmin-like activity was due to elevated levels of plasminogen activator this enzyme was assayed in four patients and was found to be negative (Table 2 ). In eight control individuals the range of plasminogen activator was 0.6-9.8 Ploug units per ml. Patient 1 had a high level of fibronectin in tear fluid (5.3 ug/ml). In controls (numbers 20, 21 and 22) the concentration of fibronectin was <1 ug/ml. Aprotinin (an inhibitor of serine proteinases), L-cysteine and heparin (inhibitors of collagenase) were tested in the assay. Aprotinin was found to inhibit effectively the proteolytic activity, L-cysteine had a minimal inhibitory effect while heparin had no effect on the activity (Table 3 ). This formed the basis for the therapeutic approach described below for the fifteen patients with proteolytic activity in tear fluid specimens.

Topical treatment with proteinase inhibitor with or without fibronectin

The first patient (case 1 in Table 3) with a chronic corneal erosion resistant to conventional therapy (antibiotics, corticosteroids) was initially treated with topical fibronectin starting on October 16. One day later the corneal erosion had an altered appearance. There was a thin layer of abnormal and cloudy epithelium at the bottom of the crater. A small epithelial scraping on October 19 confirmed the presence of epithelial cells in the wound. Tear fluid analysis revealed proteolytic activity. Topical fibronectin was, therefore, on October 22 combined with topical proteinase inhibitor (aprotinin). There was an immediate dramatic improvement in his condition so that on October 30 the patient had already visual acuity 0.5 and he was admitted to go home. On January 15 his visual acuity was 0.7 and the epithelium intact.

After the success with this index case and similar experience with the first few additional patients the following therapeutic regimen was adopted. Patients with corneal ulcers were first treated for four days with conventional therapy including antimicrobial drugs according to laboratory findings or clinical picture. If no response was seen and if proteolytic activity was detected in the tear fluid, aprotinin therapy was initiated. In some cases with low activity in the initial or later tear fluid specimens, aprotinin was combined with topical fibronectin. In addition, in certain patients, such as in a patient with bilateral acid corrosion, no proteolytic activity was detected immediately after injury. The right eye of the patient was initially treated with topical fibronectin with clear beneficial effect and epithelial healing. However, when fibronectin was applied 7 days later to the left eye, no such therapeutic effect was observed. The tear fluid was reanalyzed and now showed plasmin-like activity. In zymographic analysis the proteinase in the patient's tear fluid specimen comigrated with plasmin (data not shown). Aprotinin therapy was initiated and led to rapid epithelization. This patient will be described in detail elsewhere. However, a large proportion of patients with therapy-resistant corneal lesions of various categories (Table 2 ) had proteolytic activity and the above regimen was followed. In all fifteen patients treated to date (Table 2), this therapy has resulted in corneal epithelialization.

DISCUSSION OF RESULTS

It was found that all fifteen patients with both proteolytic activity in tear fluid and corneal lesion responded quickly to the therapy by development of covering corneal epithelium. The following patient histories merit special emphasis. The first patient (patient 1) had been previously treated for nine weeks with local and systemic antibiotics, local corticosteroids as well as with a soft contact lens without any success. This patient responded to the novel therapy promptly within 24 hours. Patient 3 with corneal erosion caused by the use of soft contact lens did not respond to the use of antibiotic ointment and a firm pad but improved rapidly after the onset of the proteinase inhibitor therapy. Patient 4 had a chronic dry eye syndrome and developed corneal ulcer in her right eye. In spite of conventional therapy with antibiotics the ulcer perforated spontaneously. The perforation was treated conservatively with soft contact lens and antibiotics together with aprotinin which led to healing. This patient and another one (data not shown) indicate that proteolytic events may play a role in perforation of corneal ulcer. Similarly, patient 10 responded in one day. The present observations may also elucidate the pathogenesis of Mooren's ulcer (patient 7), a condition of unknown etiology and notoriously progressive and therapy-resistant. The patient, who had already lost the other eye, was successfully treated initially with 20 IU/ml of aprotinin and later (20 Jan on), since the proteolytic activity was unusually high, with 40 IU/ml hourly. Within a month after onset of aprotinin therapy the ulcer has regressed into a third of its original area.

Ocular padding is the current treatment of choice for corneal erosions. However, it is a general clinical evidence that prolonged covering of the eye may sometimes have adverse effects. During this study we found that in a few patients ocular padding for more than one day was occasionally found to increase the tear fluid proteolytic activity. This was observed for patients 1 and 7 and another patient not listed in Table 4.

the proteinase(s) in tear fluid were inhibited by aprotinin, an inhibitor of serine proteinases. This finding and the comigration of major proteolytic activity with human plasmin, suggests plasmin as the principal tear fluid proteinase. The presence of collagenase activity in some corneal ulcerations has been previously recognized[25,26]. The main drugs to inhibit collagenolytic activity, thought to destroy corneal tissue, have been L-cysteine and heparin. This type of treatment was used at first in patients 1, 3 and 4 but with little or no clinical effect. The cornea of patient 4 perforated spontaneously during topical L-cysteine therapy in the absence of detectable microbial pathogens, probably due to proteolytic activity. These inhibitors of collagenase had also very little effect on the proteolytic activity of tear fluid of patients 1, 2, 8 and 9 in vitro. In keratitis caused by the opportunistic pathogen Serratia marcescens the Mr 56 000 bacterial metalloproteinase is thought to be a major pathogenic factor[27,28,29]. On the basis of the results obtained, it appears that therapeutic intervention with proteinase inhibitor could be beneficial also in these patients.

It has also been noted that when an allergen, such as birch pollen, is applied to the eye, proteolytic activity is observed in the tear fluid in about 10 minutes and the eye becomes inflamed. This provides a basis for a novel type of allergy test.

In the published report[15] on the clinical use of fibronectin, the healing of the epithelium took about 20 days. In the light of the present study it is difficult to estimate the effect of fibronectin therapy unless the tear fluid proteolytic activity is tested.

In view of the pronounced susceptibility of fibronectin to proteolytic degradation and the observation made on tear fluid proteolytic activity, it is recommended that the following regimen for therapy be used. When proteolytic activity in tear fluid is detected, firstly therapy with proteinase inhibitor should be initiated. Specific antimicrobial and/or antiallergic therapy, if indicated, should also be applied. Only if the proteolytic activity is under control, administration of fibronectin may be beneficial. No side effects of aprotinin therapy have been noticed. The longest treatment with aprotinin eye drops (patient 4 with dry eyes and spontaneous perforation) lasted five weeks and yielded good results without corneal or other complications.

Similar proteolytic activation and destruction, as described here for corneal lesions, conceivably operate in various lesions of skin and mucous membranes, such as those caused by trauma, infections and chronic disease processes[18,21,22]. Proteolytic activation is a general consequence of inflammatory processes, resulting both from tissue destruction, from activities of cells involved in host defense and in tissue repair, as well as from microbial metabolism. The adhesive glycoprotein, fibronectin, known for its sensitivity to proteolytic degradation, is unable to promote epithelial cell attachment and spreading under conditions of proteolytic activity.

In view of the clear beneficial therapeutic results of the proteinase inhibitor a large clinical project has been started to define the role of tear fluid proteinase activity and its therapeutic inhibition in corneal lesions of various etiologies. The results of the project already indicate that tear fluid proteolytic activity is as general feature of therapy-resistant sterile corneal ulcers. It will be also of interest to study what is the source and mechanism of proteolytic activation to understand and optimize the antiproteinase therapy.

As will be clearly apparent from the disclosure, the invention also resides in a therapeutic composition or preparation for the treatment of epithelial lesions, the composition or preparation containing a proteinase inhibitor, such as aprotinin. The inhibitor may be used in various forms, preferably with a physiologically acceptable carrier. Such carriers are well known in the pharmaceutical art and may include sterile solutions, ointments and the like. Examples of well known sterile solutions are sterile water, sterile saline solutions, and the like.

A dosage composition that can be used in treating an epithelial lesion, such as a corneal lesion, is one containing about 5 IU/ml to about 200 IU/ml of aprotinin. One IU of aprotinin corresponds to about 140 nanograms or about 0.14 ug aprotinin.

Where fibronectin is called for in combination with the aprotinin treatment, the fibronectin is preferably employed following treatment with aprotinin. The concentration of the fibronectin composition may range from about 10 to about 1000 ug/ml. The treatment of epithelial lesions may also include the use of corticosteroids, antimicrobial agents as is well known in the art.

Although the present invention has been described in conjunction with the preferred embodiments, it is to be understood that modifications and variations may be resorted to without departing from the spirit and scope of the invention as those skilled in the art will readily understand. Such modifications and variations are considered to be within the purview and scope of the invention and the appended claims.

TABLE 1

Tear fluid proteolytic activity in the different patient categories

| Patient group | Plasmin-like activity Positive (>0.1 ug/ml) | Plasmin-like activity Negative (<0.1 ug/ml) |
|---|---|---|
| Recurrent or chronic erosion | 7 | 1 |
| Keratitis | 16 | 11 |
| Chronic blepharitis with corneal punctate lesions | 2 | 1 |
| Contact lens lesion | 2 | |
| Contusion | 1 | |
| Mechanical erosion | | 1 |
| Post-operative cataract or transplantation | 1 | 2 |
| Total number of patients | 29 | 16 |

TABLE 2

Plasminogen activator levels in tear fluids specimens of patients and control individuals

| Patient number Treated patients | Plasminogen activator Date | Plasminogen activator PU/ml |
|---|---|---|
| 1 | 22 Oct | <0.1 |
| 2 | 1 Nov | <0.1 |
| 3 | 16 Nov | <0.1 |
| 4 | 25 Nov | <0.1 |
| Controls | | |
| 16 | 2 Dec | 9.8 |
| 17 | 2 Dec | 0.7 |
| 18 | 8 Dec | 2.4 |
| 19 | 8 Dec | 1.3 |
| 20 | 16 Oct | 0.8 |
| 21 | 18 Oct | 1.2 |
| 22 | 15 Oct | 0.6 |
| 23 | 25 Nov | 1.2 |

TABLE 3

Effect of inhibitors on the proteolytic activity in tear fluid specimens

| Sample | | Proteolytic plasmin-like activity (ug/ml) |
|---|---|---|
| Patient 1 | Tear fluid + | 11.6 |
| | aprotinin (20 IU/ml) + | <0.1 |
| | L-cysteine (0.075 M) + | 10.1 |
| | heparin (1250 IU/ml) | 11.9 |
| Patient 2 | Tear fluid + | 7.0 |
| | aprotinin (20 IU/ml) + | <0.1 |
| | L-cysteine (0.075 M) + | 7.2 |
| | heparin (1250 IU/ml) | 7.8 |
| Patient 7 | Tear fluid + | 7.6 |
| | aprotinin (10 IU/ml) | <0.1 |
| Patient 8 | Tear fluid + | 6.0 |
| | aprotinin (10 IU/ml) + | <0.1 |
| | L-cysteine (0.075 M) + | 4.9 |
| | heparin (1250 IU/ml) | 7.2 |
| Patient 9 | Tear fluid + | 6.3 |
| | aprotinin (10 IU/ml) + | <0.1 |
| | L-cysteine (0.075 M) + | 5.5 |
| | heparin (1250 IU/ml) | 6.8 |
| Patient 15 | Tear fluid + | 4.2 |
| | aprotinin (10 IU/ml) | <0.1 |

TABLE 4

Patients, laboratory data and effect of therapy

| PATIENT/INITIALS/SEX/YEAR OF BIRTH DIAGNOSIS AND MAIN SYMPTOMS | MICROBE | TEARFLUID PLASMIN-LIKE ACTIVITY Date | TEARFLUID PLASMIN-LIKE ACTIVITY ug/ml | THERAPY AND RESPONSE TO IT |
|---|---|---|---|---|
| Treated patients | | | | |
| 1 SK M 1959 Conjunctivitis vernalis, large corneal erosion for 10 weeks. | S. aureus | 22 Oct 30 Oct 10 Dec | 11.6 <0.1 <0.1 | Antibiotics and corticosteroids. With fibronectin and aprotinin, recovery started in 2 days. Epithelialization complete in 3 weeks. |
| 2 EA-H F 1945 Disciform Keratitis (history of mechanical trauma), recurrent erosion for 1 week. | None found HSV suspected | 1 Nov 25 Nov | 7.0 <0.1 | Initially antibiotics and acyclovir with no response. Recovery in 4 days with aprotinin. |
| 3 KA F 1965 Soft contact lens user, giant papillary conjunctivitis, recurrent corneal erosion for 2 days. | None found | 16 Nov 4 Dec | 6.8 <0.1 | Complete epithelialization in 48 hours following aprotinin therapy. |
| 4 EJ F 1910 Keratitis sicca, leading to corneal perforation (20 Sept) and ulcer. | None found | 25 Nov 20 Dec | 5.5 <0.1 | Little improvement with antibiotics and soft contact lens. Aprotinin promoted corneal healing which took six weeks. |
| 5 TL F 1959 Corneal transplantation (keratoconus) and fungal ulcer, irritation for 2 weeks. | Fungi | 9 Dec | 0.5 | Aprotinin, fibronectin and antifungal drugs for 2 weeks, later fibronectin only since low protease activity. Complete recovery within 4 weeks. |
| 6 SS M 1932 Ulcus corneae and pseudophacia, lesio maculea (phototoxica) long irritating stitches | None found | 2 Jan | 5.2 | First topical antibiotics and contact lens without improvement. With aprotinin and fibronectin healing in 2 weeks. |
| 7 HJ F 1922 Ulcus Mooren | None found | 8 Jan 10 Jan 16 Jan 20 Jan 22 Jan 27 Jan 30 Jan 3 Feb | 7.6 4.7 12.0 12.5 3.3 3.0 0.5 <0.1 | With antibiotics and other conventional therapy the illness progressed. With aprotinin (Jan 8) later combined with fibronectin (Jan 22) slow healing starting on Jan 27. |
| 8 MW F 1897 Ulcus corneae for 1 week | S. aureus | 6 Jan 8 Jan 29 Jan | 6.0 4.5 0.5 | During antibiotic therapy a recidive (Jan 26). After onset of aprotinin, complete healing in 12 days (Feb 9). |

TABLE 4-continued

Patients, laboratory data and effect of therapy

| PATIENT/INITIALS/SEX/YEAR OF BIRTH DIAGNOSIS AND MAIN SYMPTOMS | MICROBE | TEARFLUID PLASMIN-LIKE ACTIVITY Date | ug/ml | THERAPY AND RESPONSE TO IT |
|---|---|---|---|---|
| | | 31 Jan | 0.5 | |
| | | 14 Feb | <0.1 | |
| 9 AV F 1911<br>Deep corneal ulcer and ectropium palp. | S. aureus | 16 Jan<br>20 Jan<br>30 Jan<br>13 Feb | 6.3<br>3.0<br><0.1<br><0.1 | Topical antibiotics, operatio plastica, topical antibiotics and aprotinin, rapid epithelialization. |
| 10 JH M 1967<br>Giant papillary conjunctivitis for 4 days | None found | 20 Jan<br>22 Jan<br>24 Jan | 10.3<br>2.4<br><0.1 | First topical antibiotics. After aprotinin epithelialization in one day. |
| 11 MS F 1905<br>St. post transplantationem corneae, corneal erosion | None found | 21 Jan<br>30 Jan<br>9 Feb | 3.1<br>1.9<br><0.1 | Topical antibiotics, partial tarsorrophy and aprotinin, epithelialization in three days following aprotinin therapy. |
| 12 AP F 1914<br>Absc. corneae | Moraxella | 22 Jan<br>24 Jan<br>6 Feb | 20.0<br>12.4<br><0.1 | Antibiotics and aprotinin. Complete epithelialization in 2 weeks. |
| 13 UM M 1924<br>Herpes keratitis leading to corneal erosion and transplantation. Now new erosion. | None found | 31 Jan<br>3 Feb<br>19 Feb | 6.3<br>0.5<br><0.1 | Topical acyclovir, antibiotics and aprotinin, and after aprotinin therapy clear improvement. |
| 14 RR M 1957<br>Blepharitis chronica. | None found | 24 Jan | 3.7 | Aprotinin, condition improved in 1 week. |
| 15 RB M 1963<br>Conjunctivitis vernalis, punctate erosion.<br>Controls | None found | 7 Feb | 4.2 | Aprotinin, condition improved in 5 days. |
| 16 F 1921 | Glaucoma | 2 Dec | <0.1 | |
| 17 F 1905 | Glaucoma | 2 Dec | <0.1 | |
| 18 F 1929 | Glaucoma | 8 Dec | <0.1 | |
| 19 F 1932 | Glaucoma | 8 Dec | <0.1 | |
| 20 F 1950 (Healthy nurse) | | 16 Oct | <0.1 | |
| 21 F 1946 (Scientist) | | 18 Oct | <0.1 | |
| 22 M 1958 (Scientist) | | 15 Oct | <0.1 | |
| 23 F 1958 (Technician) | | 25 Nov | <0.1 | |

<sup>a</sup>For additional data see text

APPENDIX

1: Hynes R O, Yamada K M. Fibronectins: Multifunctional modular glycoproteins, J Cell Biol 1982; 95: 369-377.

2: Mosesson M W, Amrani D L. The structure and biologic activities of plasma fibronectin. Blood 1980; 56 (2): 145-158.

3: Vaheri A, Salonen E-M, Vartio T. Fibronectin in formation and degradation of the pericellular matrix. In: Evered D, Whelan J, eds. Fibrosis (Ciba Foundation Symp no 114). London: Pitman, pp. 111-126, 1985.

4: Tervo T, Sulonen J, Valtonen S, Vannas A, Virtanen I. Distribution of fibronectin in human and rabbit corneas. Exp Eye Res (in press).

5: Engvall E, Ruoslahti E. Binding of soluble form of fibroblast surface protein, fibronectin, to collagen. Int J Cancer 1977; 20: 1-5.

6: Jilek F, Hüormann H. Fibronectin (cold insoluble globulin) VI influence of heparin and hyaluronic acid on the binding of native collagen. Hoppe-Seyler's Z Physiol Chem 1979; 360: 597-603.

7: Yamada K M, Kennedy D W, Kimata K, Pratt R M. Characterization of fibronectin interaction with glycosaminoglycans and identification of active proteolytic fragments. J Biol Chem 1980; 255: 6055-6063.

8: Salonen E-M, Vartio T, Hedman K, Vaheri, A Binding of fibronectin by the actue-phase reactant C-reactive protein. J Biol Chem 1984; 259: 1496-1514.

9: Salonen E-M, Saksela O, Vartio T, Vaheri A, Nielen L, Zeuthen J. Plasminogen and tissue-type plaminogen activator bind to immobilized fibronectin. J Biol Chem 1985; 260: 12,302-07.

10: Piersbacher M D, Ruoslahti E. Cell attachment activity of fibronectin can be cuplicated by small synthetic fragments of the molecule. Nature (Lond) 1984; 309: 30-33.

11: Kurkinen M. Alitalo K, Vaheri A, Stenman S, Saxen L. Fibronectin in the development of chick eye. Dev Biol 1979; 69: 589-600.

12: Vaheri A, Salonen E-M, Vartio T, Hedman K, Stenman S. Fibronectin and tissue injury. In: N. Woolf, eds. Biology and Pathology of the Vessel Wall. Eastbourne: Praeger, pp. 161-171, 1983.

13: Saksela O, Alitalo K, Kiistala U, Vaheri A. Baal lamina components in experimentally induced skin blisters. J Invest Dermatol 1981; 77: 283-286.

14: Fujikawa L S, Foster C S, Harrist T J, Lanigan J M, Colvin R B. Fibronectin in healing rabbit corneal wounds Lab Invest 1981; 45: 120-129.

15: Nishida T, Ohashi Y, Inove Y, Nikagawa S, Awata T, Suda T, Manable R. Dynamics of fibronectin in corneal wound healing: immunohistochemical study of experimental bullous keratopathy in rabbits. Cornea 1982; 1:311-317.

16: Harnisch J-P, Sinha P K. Fibronectin: Eine Behandlungsmöglichkeit therapieresistenter Hornhautulzera. Klin Mb Augenheilk 1985; 187: 53-56.

17: Vartio T, Seppä H, Vaheri A. Susceptibility of soluble and matrix fibronectins to degradation by tissue proteinases, mast cell chymase and cathepsin G. J Biol Chem 1981; 256: 471-477.

18: Danø K, Andreasen P A, Grøndahl-Hansen J, Kristensen P, Nielsen L S, Skriver L. Plasminogen activators and cancer. Adv Cancer Res 1985; 44: 139–266.

19: Harris E D, Cartwright E C. Mammalian collagenases. In: A J Barrett, ed. Proteinases in Mammalian Cells and Tissues. pp. 249–283. Amsterdam: North-Holland, 1977.

20: Sellers A, Cartwright E, Murphy G, Reynolds J J. Evidence that latent collagenases are enzyme-inhibitor complexes. Biochem J 1977; 163: 303–307.

21: Reich E, Rifkin D B, Shaw E. (eds.) Proteases and Biological Control. 1021 pages. Cold Spring Harbor Laboratory, 1975.

22: Barrett A J. The Cellular Proteinases—A Broad View. In: P Sträuli, A J Barrett, A Baici, eds. Proteinases and Tumor Invasion. pp. 59–67. New York: Raven Press, 1980.

23: Saksela O. Radial caseinolysis in agarose: a simple method for detection of plasminogen activator in the presence of inhibitory substances and serum. Anal Biochem 1981; 111: 276–282.

24: Salonen E-M, Vartio T, Miggiano V. Stähli C, Takacs B, Virgallita G, De Petro G, Barlati S, Vaheri A. A rapid and highly sensitive solid-phase enzyme immunoassay specific for human fibronectin using a characterized monoclonal antibody. J Immunol Methods 1984; 72: 145–156.

25: Slansky H H, Dohlman C H. Collagenase and the cornea. Survey Ophthal 1970; 14: 402–415.

26: Gordon J M, Bauer E A, Eisen A Z. Collagenase in human cornea. Arch Ophthalmol 1980; 98: 341–345.

27: Lyerly D, Kreger A. Purification and characterization of a Serratia marcenscens metalloprotease. Infection and Immunity 1979; 24: 411–421.

28: Matsumoto K, Maeda H, Takata K, Kamata R, Okamura R. Purification and characterization of four proteases from a clinical isolate of Serratia marcescens kums 3958. J Bacteriol 1984; 157: 225–232.

29: Kamata R, Matsumoto K, Okamura R, Yamamoto T, Hiroshi M. The serratial 56k proteases as a major pathogenic factor in serratial keratitis. Ophthalmol 1985; 92: 1452–1459.

What is claimed is:

1. A method of treating a patient having an epithelial lesion of the eye due to plasmin-induced epithelial destruction and characterized by the presence of plasmin in tear fluids which comprises, applying to said eye lesion a therapeutically effective amount of aprotinin in the form of a physiologically acceptable preparation.

2. A method of treating a patient having a corneal lesion of the eye due to plasmin-induced corneal destruction and characterized by the presence of plasmin in tear fluids which comprises, applying to said eye lesion a therapeutically effective amount of aprotinin in the form of a physiologically acceptable preparation.

3. A method of treating a patient having an epithelial lesion of the eye due to plasmin-induced epithelial destruction and characterized by the presence of plasmin in tear fluids which comprises, applying to said eye lesion a pharmaceutical preparation of aprotinin containing about 5 IU/ml to about 200 IU/ml aprotinin.

4. The method of claim 3, wherein said epithelial lesion is a corneal lesion.

5. A method of treating a patient having an epithelial lesion of the eye due to plasmin-induced epithelial destruction and characterized by the presence of plasmin in tear fluids which comprises, applying to said eye lesion a therapeutically effective amount of aprotinin in the form of a physiological acceptable preparation in combination with the application of a therapeutically effective amount of fibronectin.

6. A method of treating a patient having an epithelial lesion of the eye due to plasmin-induced epithelial destruction and characterized by the presence of plasmin in tear fluids which comprises, applying to said lesion a pharmaceutical preparation containing about 5 IU/ml to about 200 IU/ml aprotinin in combination with the application of a pharmaceutical preparation containing about 10 ug/ml to about 1000 ug/ml fibronectin.

7. The method of claim 6, wherein said epithelial lesion is a corneal lesion.

* * * * *